US010299679B2

United States Patent
Yang (10) Patent No.: US 10,299,679 B2
(45) Date of Patent: May 28, 2019

(54) METHOD AND SYSTEM FOR WIRELESSLY AND PASSIVELY MEASURING TEMPERATURE AND DEVICES FORMING THE SYSTEM

(71) Applicant: Shenzhen Zhiying Technologies Co., Ltd., Shenzhen, Guangdong (CN)

(72) Inventor: Song Yang, Guangdong (CN)

(73) Assignee: Shenzhen Zhiying Technologies Co., Ltd., Shenzhen (CN)

( * ) Notice: Subject to any disclaimer, the term of this patent is extended or adjusted under 35 U.S.C. 154(b) by 250 days.

(21) Appl. No.: 15/193,191

(22) Filed: Jun. 27, 2016

(65) Prior Publication Data

US 2016/0302668 A1    Oct. 20, 2016

Related U.S. Application Data (63) Continuation of application No. PCT/CN2014/094864, filed on Dec. 24, 2014.

(30) Foreign Application Priority Data

Dec. 25, 2013 (CN) .......................... 2013 1 0728107

(51) Int. Cl.
*G01K 11/22* (2006.01)
*G01K 7/00* (2006.01)
(Continued)

(52) U.S. Cl.
CPC .............. *A61B 5/0008* (2013.01); *A61B 5/01* (2013.01); *G01K 7/32* (2013.01); *H02J 7/025* (2013.01); *H02J 17/00* (2013.01); *H02J 50/20* (2016.02)

(58) Field of Classification Search
USPC ................................ 374/117, 100, 166, 112
See application file for complete search history.

(56) References Cited

U.S. PATENT DOCUMENTS

| 2006/0038626 | A1  | 2/2006 | Duval et al. |
| 2007/0104298 | A1* | 5/2007 | Filipovic ................... H03J 7/10 |
| | | | 375/344 |

(Continued)

FOREIGN PATENT DOCUMENTS

| CN | 2286874 Y | 7/1998 |
| CN | 201852639 U | 6/2011 |

(Continued)

OTHER PUBLICATIONS

International Search Report of PCT Patent Application No. PCT/CN2014/094864 dated Mar. 24, 2015.

(Continued)

*Primary Examiner* — Mirellys Jagan (57) ABSTRACT

The present disclosure provides a method and a system for wirelessly and passively measuring temperature and devices forming the system. The method includes: receiving an energy feedback radio frequency (RF) signal by a temperature measuring end; converting the energy feedback RF signal into electric energy and storing the electric energy; and starting the temperature measuring end after obtaining the electric energy, and transmitting a RF signal under the current temperature to a terminal, and calculating the current temperature through the terminal. The method, the system and the devices forming the system provided in the present disclosure are capable of activating the crystal oscillator or the ceramic oscillator wirelessly and passively, therefore, the method, the system and the devices can be used to wirelessly and passively measure temperature, which is convenient.

6 Claims, 3 Drawing Sheets

(51) Int. Cl.
*G01K 3/00* (2006.01)
*A61B 5/00* (2006.01)
*H02J 7/02* (2016.01)
*H02J 50/20* (2016.01)
*A61B 5/01* (2006.01)
*G01K 7/32* (2006.01)
*H02J 17/00* (2006.01)

(56) References Cited

U.S. PATENT DOCUMENTS

| | | | | |
|---|---|---|---|---|
| 2007/0205916 A1* | 9/2007 | Blom | ............... | G01K 7/01 |
| | | | | 340/870.17 |
| 2010/0240325 A1* | 9/2010 | Li | ............... | H04W 52/52 |
| | | | | 455/84 |
| 2012/0209558 A1* | 8/2012 | Wilcox | ............... | H03B 5/36 |
| | | | | 702/130 |

FOREIGN PATENT DOCUMENTS

| | | |
|---|---|---|
| CN | 102713547 A | 10/2012 |
| CN | 102938897 A | 2/2013 |
| CN | 102980677 A | 3/2013 |
| CN | 203014467 U | 6/2013 |
| CN | 103750826 A | 4/2014 |
| CN | 203988002 U | 12/2014 |
| JP | 2012-7963 A | 1/2012 |

OTHER PUBLICATIONS

1st Office Action of counterpart Chinese Patent Application No. 201310728107.3 dated Jul. 13, 2015.
2nd Office Action of counterpart Chinese Patent Application No. 201310728107.3 dated Aug. 23, 2016.

* cited by examiner

METHOD AND SYSTEM FOR WIRELESSLY AND PASSIVELY MEASURING TEMPERATURE AND DEVICES FORMING THE SYSTEM

CROSS-REFERENCE TO RELATED APPLICATIONS

The present application is a Continuation application of PCT application No. PCT/CN2014/094864 filed on Dec. 24, 2014, which claims the benefit of Chinese Patent Application No. 201310728107.3 filed on Dec. 25, 2013, the contents of which are hereby incorporated by reference.

FIELD OF THE INVENTION

The present disclosure generally relates to the field of temperature measurement and, more particularly, relates to a method and a system for wirelessly and passively measuring temperature and devices forming the system.

BACKGROUND

Main human body features include body temperature, blood pressure, pulse, respiration, etc. During these human body features, body temperature is a very important physiological signal which forms an important part of the measuring and monitoring of the medical care work. The measuring accuracy in medical level is 0.2° C. Nowadays, the mercury thermometer is still used as the medical temperature measuring tool. However, the mercury thermometer has hidden dangers in safety and environment pollution. The hidden safety danger includes cross-infection and being cut by the glass when the glass of the mercury thermometer breaks. The hidden danger in environment pollution may arise when the mercury thermometer breaks since the mercury is a toxic substance. Moreover, it takes long time to measure the temperature using the mercury thermometer and it is troublesome to read the data, which affects the work efficiency.

Since the technology of quartz crystal oscillator has the advantages including strong stability and rapid measurement speed, the technology of quartz crystal oscillator can be used to measure temperature by replacing the mercury thermometer. However, at present, during the temperature measurement, extra electric energy needs to be provided to activate the quartz crystal oscillator, resulting in the complex usage of the quartz crystal oscillator. Thus, it is inconvenient for the user to use the technology of quartz crystal oscillator.

BRIEF SUMMARY OF THE DISCLOSURE

The main purpose of the present disclosure is to provide a method and a system for wirelessly and passively measuring temperature and devices forming the system, which can conveniently and rapidly measure temperature.

One aspect of the present disclosure provides a method for wirelessly and passively measuring temperature, including:
  receiving an energy feedback radio frequency (RF) signal by a temperature measuring end;
  converting the energy feedback RF signal into electric energy and storing the electric energy; and
  starting the temperature measuring end after obtaining the electric energy, transmitting a RF signal under the current temperature to a terminal, and calculating the current temperature through the terminal.

Preferably, the temperature measuring end includes a crystal oscillator circuit; the crystal oscillator circuit starts after obtaining the electric energy, and transmits the RF signal under the current temperature.

Preferably, the step of converting the energy feedback RF signal into electric energy and storing the electric energy includes:
  receiving the energy feedback RF signal through a RF receiving circuit by the temperature measuring end, and storing the energy of the feedback RF signal into a storage capacitor by the RF receiving circuit.

Preferably, after the step of starting the temperature measuring end after obtaining the electric energy, and transmitting a RF signal under the current temperature to a terminal, and calculating the current temperature through the terminal, the method further includes:
  sending the calculated current temperature to a remote terminal through network.

One aspect of the present disclosure provides a wireless and passive temperature sensing device, including a RF receiving circuit, a storage capacitor, and a crystal oscillator circuit; the RF receiving circuit receives an energy feedback RF signal from an energy feedback device, and converts the energy feedback signal into electric energy; the electric energy is stored into the storage capacitor; and after a voltage of the storage capacitor reaches a suitable level, the crystal oscillator is started to transmit a RF signal under the current temperature to an external receiving and processing device.

Preferably, the wireless and passive temperature sensing device further includes a first house; the RF receiving circuit, the storage capacitor, and the crystal oscillator circuit are configured inside the first house; one side of the first house corresponding to the crystal oscillator is made of thermal conductive material; or, one side of the first house corresponding to the crystal oscillator forms an opening through which the crystal oscillator circuit protrudes from the side of the first house.

Preferably, the wireless and passive temperature sensing device further includes a connection structure; the connection structure includes at least one protrusion configured on a peripheral side of the first house and a through hole formed on each of the at least one protrusion; or, the connection structure includes a Velcro configured on the first house; or, the connection structure includes a locking device configured on the first house.

One aspect of the present disclosure provides an energy feedback device, including a first temperature compensation crystal oscillator and a RF power amplifier; a RF signal from the first temperature compensation crystal oscillator is amplified by the RF power amplifier and is further transmit to a wireless and passive temperature sensing device. One aspect of the present disclosure provides a receiving and processing device, comprising a temperature compensation crystal oscillator, a RF receiving amplifier, and a signal processor; the RF receiving amplifier receives a RF signal under the current temperature transmit by a wireless and passive temperature sensing device and outputs the RF signal into the signal processor; and the signal processor calculates the current temperature according to an inherent frequency of the temperature compensation crystal oscillator and the received RF signal under the current temperature.

Preferably, the receiving and processing device further includes a network unit connected to the signal processor for receiving and transmitting data through network.

One aspect of the present disclosure provides an energy feedback receiving and processing device, including a temperature compensation crystal oscillator, a RF power amplifier, a RF receiving amplifier, and a signal processor; a RF signal from the temperature compensation crystal oscillator is amplified by the RF power amplifier and is further transmit to a wireless and passive temperature sensing device; the RF receiving amplifier receives the RF signal under the current temperature from the wireless and passive temperature sensing device and outputs the RF signal to the signal processor; and the signal processor calculates the current temperature according to an inherent frequency of the temperature compensation crystal oscillator and the received RF signal under the current temperature.

Preferably, the energy feedback receiving and processing device further includes a second house; the temperature compensation crystal oscillator, the RF power amplifier, the RF receiving amplifier, and the signal processor are configured in the second house.

Preferably, the energy feedback receiving and processing device further includes a network unit connected to the signal processor for receiving and transmitting data through network.

One aspect of the present disclosure provides a system for wirelessly and passively measuring temperature, comprising a wireless and passive temperature sensing device, an energy feedback device, and a receiving and processing device;

the energy feedback device includes a temperature compensation crystal oscillator and a RF power amplifier, and a RF signal from the temperature compensation crystal oscillator is amplified by the RF power amplifier and is further transmit to the wireless and passive temperature sensing device;

the wireless and passive temperature sensing device includes a RF receiving circuit, a storage capacitor, and a crystal oscillator circuit; the RF receiving circuit receives an energy feedback RF signal from the energy feedback device; energy of the RF signal is stored into the storage capacitor; after the voltage of the storage capacitor reaches a suitable level, the crystal oscillator circuit is activated to transmit the RF signal under the current temperature from the crystal oscillator circuit to the receiving and processing device;

the receiving and processing device includes a temperature compensation crystal oscillator, a RF receiving amplifier, and a signal processor; the RF receiving amplifier receives the RF signal under the current temperature from the wireless and passive temperature sensing device and outputs the RF signal into the signal processor; and the signal processor calculates the current temperature according to an inherent frequency of the second temperature compensation crystal oscillator and the received RF signal under the current temperature.

Preferably, the energy feedback device and the receiving and processing device share one temperature compensation crystal oscillator.

Preferably, the wireless and passive temperature sensing device includes a first house; the RF receiving circuit, the storage capacitor, and the crystal oscillator circuit are configured in the first house; and one side of the house corresponding to the crystal oscillator circuit is made of thermal conductive material; or, one side of the first house forms an opening through which the crystal oscillator protrudes from the side of the house.

Preferably, the receiving and processing device further includes a network unit connected to the signal processor for receiving and transmitting data through network.

Compared with the current temperature measuring method which needs to be connected to an electric wire for providing electric energy to activate the crystal oscillator and is troublesome, the method and the system and devices forming the system for wirelessly and passively measuring temperature uses are capable of activating the crystal oscillator or the ceramic oscillator wirelessly and passively, therefore, the method, the system and the devices can be used to wirelessly and passively measure temperature, which is convenient. Also, the method, the system, and the devices can be applied in medical filed by replacing the mercury thermometer without the danger in cross infection, breaking of the glass, and environment pollution, as well as improve the working efficiency of the medical care personnel.

The realization of the object, features, and advantages of the present disclosure are given in further detail in combination with the embodiments with reference to the accompanying drawings.

DETAILED DESCRIPTION

It should be understood that the embodiments described herein are only used to explain the present disclosure rather than to limit the present disclosure.

Figure 1:
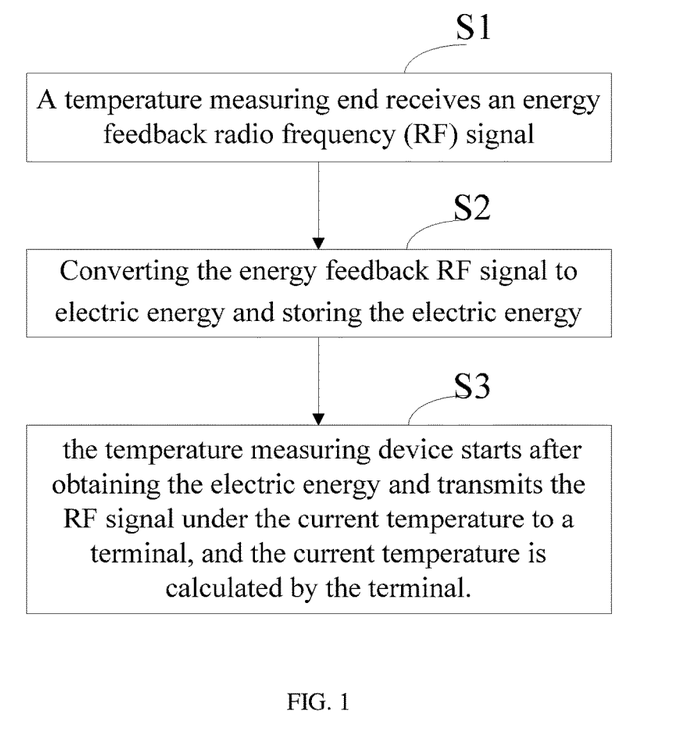
FIG. 1 illustrates a flow chart of a method for wirelessly and passively measuring temperature consistent with disclosed embodiments.

Referring to FIG. 1, a method for wirelessly and passively measuring temperature according an embodiment is provided. The method includes steps as followed.

Step S1, a temperature measuring end receives an energy feedback radio frequency (RF) signal. The temperature measuring end can be a wireless and passive temperature sensing device including a crystal oscillator circuit having a crystal oscillator. An oscillating frequency of the crystal oscillator depends on the resonant frequency of the crystal. Since the change of the resonant frequency is only affected by the temperature of the crystal and the crystal itself, therefore, if the crystal oscillator is used for transmitting the RF signal, the RF signal corresponds to the current temperature. The temperature sensing speed of the crystal oscillator is rapid, and the frequency of the RF signal of the crystal oscillator is decided by the temperature and the oscillator itself, thus, the temperature can be rapidly and accurately measured by using the crystal oscillator. In some embodiments, the crystal oscillator circuit can be a quartz crystal oscillator circuit or a ceramic crystal oscillator circuit.

Step S2, converting the energy feedback RF signal into electric energy and storing the electric energy. The temperature measuring end receives the energy feedback RF signal through a RF receiving circuit which converts the energy feedback RF signal into electric energy. The electric energy is stored into a storage capacitor until the voltage of the storage capacitor goes up to a suitable level capable of providing working electric energy for the crystal oscillator circuit. The suitable level of the voltage of the storage capacitor means that, the voltage of the storage capacitor is enough for the crystal oscillator to work for a predetermined period. When the voltage of the storage capacitor is less than the voltage needed by the crystal oscillator circuit, the crystal oscillator circuit stops working. In this way, the temperature measuring end can work normally without being connected to an electric wire or a power supply cell. This ensures the temperature measuring end to be small and portable, and thus the temperature measuring end can be placed at the to-be-measured point at any time without affecting the situation of the to-be-measured point. For example, body temperature can be measured by placing the temperature measuring end inside the underwear of the user without affecting daily life of the user. Based on this, the temperature measuring end can be used passively, which allows the user to neglect the existence of the temperature measuring end and the temperature to be measured easily. The RF signal is generally transmit by the energy feedback device. The energy feedback device includes a first temperature compensation crystal oscillator and a RF power amplifier. The RF signal from the temperature compensation crystal oscillator is amplified by the RF power amplifier and then is transmit to the wireless and passive temperature sensing device.

Step S3, the temperature measuring device starts after obtaining the electric energy and transmits the RF signal under the current temperature to a terminal, and the current temperature is calculated by the terminal. The terminal can be an electric device which is capable of receiving the RF signal under the current temperature and calculating the current temperature based on the RF signal. The terminal is typically a receiving and processing device, including a temperature compensation crystal oscillator, a RF receiving amplifier, and a signal processor. The RF receiving amplifier receives the RF signal under the current temperature sent from the wireless and passive temperature sensing device and outputs the signal to the signal processor. The signal processor calculates the current temperature according to the inherent frequency of the temperature compensation crystal oscillator and the received RF signal.

In an embodiment, the method for wirelessly and passively measuring temperature further includes step S4: the terminal sends the calculated current temperature to a remote terminal through network. Through this step, the calculated temperature can be sent to different users which are not present during the measurement process. For example, in the hospital, the nurse or the patient can send the measured temperature to the doctor through network, allowing the doctor to obtain the body temperature in time, which is convenient and rapid.

The method for wirelessly and passively measuring temperature provided in the disclosure is capable of wirelessly activating the crystal oscillator or ceramic oscillator by using the converting method from the RF signal to the electric energy, and thus capable of activating the crystal oscillator or the ceramic oscillator wirelessly and passively. Therefore, the method can be used conveniently and can be applied in medical filed. The accuracy of the device applying the method can reach 0.2° C. and thus is capable of replacing the mercury thermometer without the danger in cross infection, breaking of the glass, and environment pollution. Meanwhile, the device can improve the working efficiency of the medical care personnel.

Figure 2:
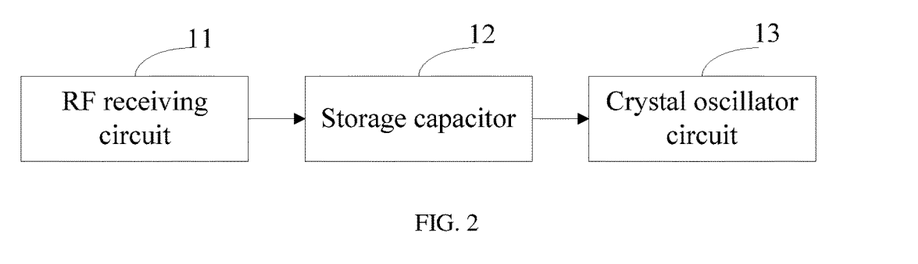
FIG. 2 illustrates a schematic diagram of a wireless and passive temperature sensing device consistent with disclosed embodiments.

Referring to FIG. 2, a wireless and passive temperature sensing device according to an embodiment is provided, including a RF receiving circuit 11, a storage capacitor 12, and a crystal oscillator circuit 13. The RF receiving circuit 11 receives an energy feedback RF signal from an energy feedback device and converts the RF signal to electric energy. The electric energy is stored into/in the storage capacitor 12. After the voltage of the storage capacitor 12 reaches a suitable level, the crystal oscillator circuit 13 starts to transmit a RF signal under the current temperature to an external receiving and processing device. The suitable level of the voltage of the storage capacitor 12 means that, the voltage of the storage capacitor 12 is enough for the crystal oscillator to work for a predetermined period. Different storage capacitors with different storage capacities can be used according to different requirements. The crystal oscillator circuit 13 can be a ceramic crystal oscillator circuit or a quartz crystal oscillator circuit. The wireless and passive temperature sensing device is configured without a structure for being connected to an external power supply and without space for receiving a battery, thus, the wireless and passive temperature sensing device can have a relatively small size for having less components, making the device be small and portable. This allows the user to place the wireless and passive temperature sensing device on any position such as on the underwear, pants, or the armpit since the wireless and passive temperature sensing device may not affect daily life of the user, which improves the temperature measuring experience of the wireless and passive temperature sensing device.

In some embodiments, the withstand voltage of the storage capacitor 12 is 2.7 V, and the capacitance of the storage capacitor 12 is 2200 uF. The storage capacitor is environmental-friendly and safe, and the quantity of electricity stored in the storage capacitor 12 is enough for the crystal oscillator circuit to work for more than 100 milliseconds.

Figure 3:
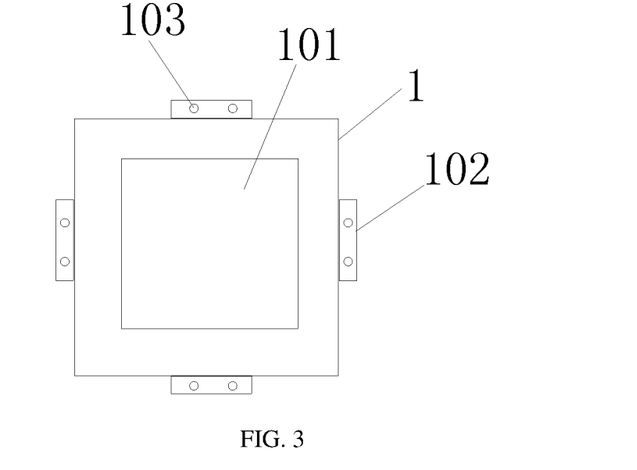
FIG. 3 illustrates a schematic view of a first house of the device of FIG. 2.

Referring to FIG. 3, the wireless and passive temperature sensing device further includes a first house 1. The RF receiving circuit 11, the storage capacitor 12, and the crystal oscillator circuit 13 are configured in the first house 1. One side of the first house 1 corresponding to the crystal oscillator circuit 13 is made of thermal conductive material, which ensures that the crystal oscillator 13 is capable of sensing the temperature more quickly and the temperature is closer to the real value. Alternatively, the side of the house 1 corresponding to the crystal oscillator 13 can form an opening 101 through which the crystal oscillator circuit 13 protrudes from the side of the house 1. At least one protrusion 102 is configured on the peripheral side of the house 1. A through hole 103 is defined in each protrusion 102. The configuration of the protrusion 102 and the through hole 103 allows the wireless and passive temperature sensing device to be secured to the underwear or the pants of the user. In some embodiments, Velcro can be configured on the first house 1 such that the device can be directly pasted to the underwear or pants of the user. In other embodiments, a locking component such as a fastener can be configured on the first house 1 to be connected to the opening formed in the underwear or pants of the user, thus the device can be secured to the underwear or pants of the user by using a fastener.

Figure 4:
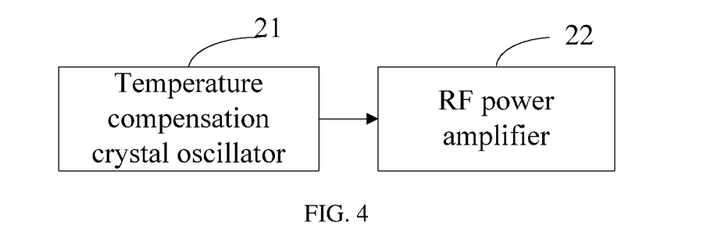
FIG. 4 illustrate a schematic diagram of an energy feedback device consistent with disclosed embodiments.

Referring to FIG. 4, an energy feedback device according to an embodiment is provided, including a temperature compensation crystal oscillator 21 and a RF power amplifier 22. A RF signal from the temperature compensation crystal oscillator 21 is amplified by the RF power amplifier 22 and is further transmit to the wireless and passive temperature sensing device. The energy feedback device may further include other supplementary components such as a power supply. The energy feedback device generates the RF signal having a special frequency through the temperature compensation crystal oscillator 21 which is transmit to the wireless and passive temperature sensing device after being amplified by the RF power amplifier, thus, the wireless and passive temperature sensing device can obtain enough energy requiring for starting up. Furthermore, the energy feedback device and the temperature sensing device are wirelessly connected, which is convenient.

Figure 5:
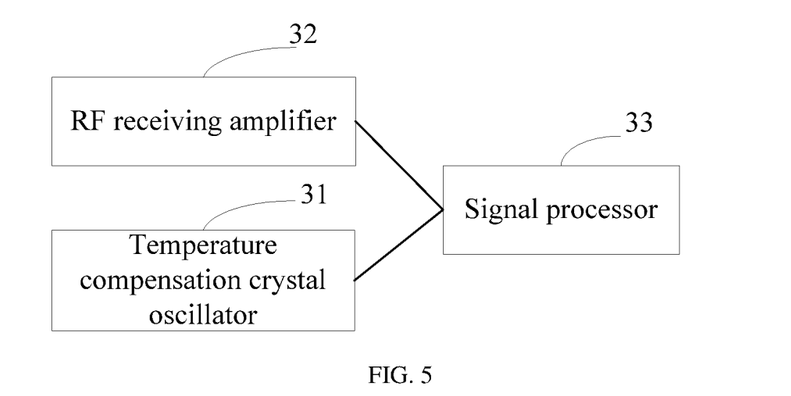
FIG. 5 illustrates a schematic diagram of a receiving and processing device consistent with disclosed embodiments.

Referring to FIG. 5, a receiving and processing device according to an embodiment is provided, including a temperature compensation crystal oscillator 31, a RF receiving amplifier 32, and a signal processor 33. The RF receiving amplifier 32 receives the RF signal under the current temperature from the wireless and passive temperature sensing device and outputs the RF signal to the signal processor 33. The signal processor 33 calculates the current temperature according to the inherent frequency of the temperature compensation crystal oscillator 31 and the received RF signal under the current temperature. Since the resonant frequency of the temperature compensation crystal oscillator 31 is fixed, by comparing the resonant frequency of the temperature compensation crystal oscillator 31 with the frequency of the RF signal sent from the crystal oscillator circuit of the wireless and passive temperature sensing device, the signal processor 33 can analyze the temperature information contained in the offset of the frequency of the RF signal sent from the crystal oscillator circuit, to obtain the current temperature. The temperature can be calculated according to the following method: the signal processor 33 is provided with a data list containing different temperatures corresponding to different frequency offsets; when a frequency offset is analyzed, looking up the corresponding temperature directly in the data list. For example, the frequency of the temperature compensation crystal oscillator 31 of the receiving and processing device is 100 MHZ, and the frequency of the RF signal output thereby is always 100 MHZ, which remains unchanged with temperature; the frequency of the RF signal sent from the wireless and passive temperature sensing device is also 100 MHZ; however, without temperature compensation, the frequency of the RF signal from the wireless and passive temperature sensing device may change 50 HZ while the temperature changes 1° C. For example, if the frequency of the RF signal is 100000000 HZ when the temperature is 24° C., then the frequency would be 100000050 HZ when the temperature is 25° C. and would be 100000100 HZ when the temperature is 26° C., and so on. Thus, the current temperature can be obtained according to the frequency of the RF signal from the wireless and passive temperature sensing device.

In some embodiments, the receiving and processing device may further include a network unit connected to the signal processor 33 for receiving and transmitting data through network. The calculated temperature can be sent to other users who are not present during the measurement through network. For example, in the hospital, the nurse or the patient can send the measured temperature to the doctor through network, allowing the doctor to obtain the temperature features of the patient, which is convenient and fast.

Figure 6:
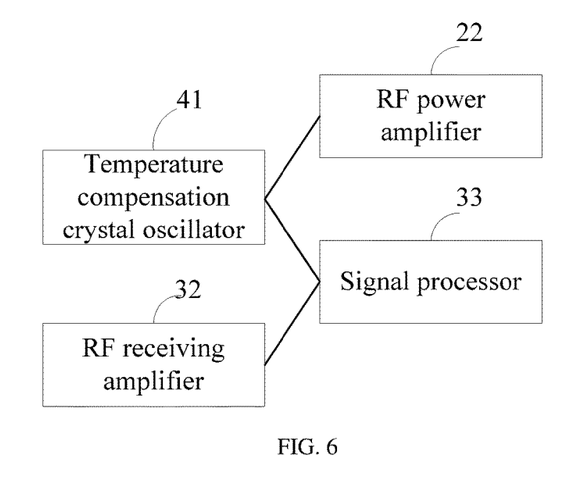
FIG. 6 illustrates a schematic diagram of an energy feedback receiving and processing device consistent with disclosed embodiments.

Referring to FIG. 6, an energy feedback receiving and processing device according to an embodiment is provided, including a temperature compensation crystal oscillator 41, a RF power amplifier 22, a RF receiving amplifier 32, and a signal processor 33. The RF signal from the temperature compensation crystal oscillator 41 is amplified by the RF power amplifier 22 and is further transmit to the wireless and passive temperature sensing device. The RF receiving amplifier 32 receives the RF signal under the current temperature sent from the wireless and passive temperature sensing device and outputs the signal to the signal processor 33. The signal processor 33 calculates the current temperature according to the inherent frequency of the temperature compensation crystal oscillator 41 and the received RF signal. The difference between the integration of the receiving and processing device and the energy feedback device provided in the above embodiment and the energy feedback receiving and processing device provided in the embodiment lies in that, the integration of the receiving and processing device and the energy feedback device includes two temperature compensation crystal oscillators 21 and 31, while the energy feedback receiving and processing device only includes one temperature compensation crystal oscillator 41. The temperature compensation crystal oscillator 41 provides the energy feedback RF signal having a special frequency as well as the frequency required by the signal processor 33.

In some embodiments, the energy feedback receiving and processing device further includes a second house. The temperature compensation crystal oscillator 41, the RF power amplifier 22, the RF receiving amplifier 32, and the signal processor 33 are configured in the second house to be an integration one which can be conveniently used and prevents some component from being lost easily.

Figure 7:
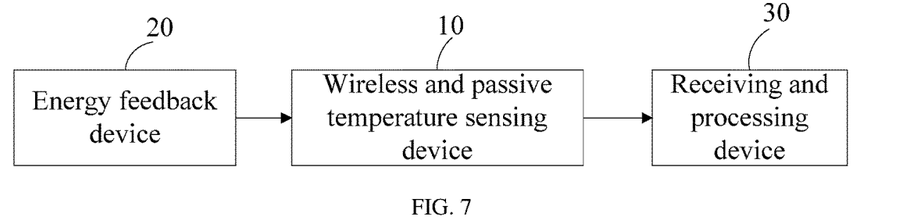
FIG. 7 illustrates a schematic diagram of a system for wirelessly and passively measuring temperature consistent with a first embodiment.

Referring to FIG. 7, a system for wirelessly and passively measuring temperature is provided according to an embodiment, including a wireless and passive temperature sensing device 10, an energy feedback device 20, and a receiving and processing device 30.

The energy feedback device 20 includes a temperature compensation crystal oscillator 21 and a RF power amplifier 22. A RF signal from the temperature compensation crystal oscillator 21 is amplified by the RF power amplifier 22 and is further transmit to the wireless and passive temperature sensing device 10.

The wireless and passive temperature sensing device 10 includes a RF receiving circuit 11, a storage capacitor 12, and a crystal oscillator circuit 13. The RF receiving circuit 22 receives an energy feedback RF signal from the energy feedback device 10 and converts the RF signal to electric energy. The electric energy is stored into/in the storage capacitor 12. After the voltage of the storage capacitor 12 reaches a suitable level, the crystal oscillator circuit 13 is activated to transmit a RF signal under the current temperature to the receiving and processing device 30. The wireless and passive temperature sensing device 10 is configured without a structure for being connected to an external power supply and without space for receiving a battery, thus, the device can have a relatively small size for having less components, making the device be small and portable. This allows the user to place the device on any position such as on the underwear, pants, or the armpit since the device may not affect daily life of the user, which improves the temperature measuring experience of the system.

The receiving and processing device 30 includes a temperature compensation oscillator 31, a RF receiving amplifier 32, and a signal processor 33. The RF receiving amplifier 32 receives the RF signal under the current temperature sent from the wireless and passive temperature measuring device 10 and outputs the signal to the signal processor 33. The signal processor calculates the current temperature according to the inherent frequency of the temperature compensation crystal oscillator 31 and the RF signal under the current temperature. Since the resonant frequency of the temperature compensation crystal oscillator 31 is fixed, by comparing the resonant frequency of the temperature compensation crystal oscillator 31 with the frequency of the RF signal sent from the crystal oscillator circuit of the wireless and passive temperature sensing device, the signal processor 33 can analyze the temperature information contained in the offset of the frequency of the RF signal sent from the crystal oscillator circuit, to obtain the current temperature. The temperature can be calculated according to the following method: the signal processor 33 is provided with a data list containing different temperatures corresponding to different frequency offsets; when a frequency offset is analyzed, looking up the corresponding temperature directly in the data list.

In some embodiments, the withstand voltage of the storage capacitor 12 of the wireless and passive temperature sensing device 10 is 2.7 V, and the capacitance of the storage capacitor 12 is 2200 uF. The storage capacitor is environmental-friendly and safe, and the discharging process of the storage capacitor 12 can last for more than 100 milliseconds.

In some embodiments, the wireless and passive temperature sensing device further includes a first house 1. The RF receiving circuit 11, the storage capacitor 12, and the crystal oscillator 13 are configured in the first house 1. One side of the first house 1 corresponding to the crystal oscillator circuit 13 is made of thermal conductive material, which ensures that the crystal oscillator 13 receives the temperature more quickly and the temperature is closer to the real value. Alternatively, the side of the house 1 corresponding to the crystal oscillator 13 can form an opening 101 through which the crystal oscillator circuit 13 protrudes from the side of the house 1. At least one protrusion 102 is configured on the peripheral side of the house 1. A through hole 103 is defined in each protrusion 102. The configuration of the protrusion 102 and the through hole 103 allows the device to be secured to the underwear or the pants of the user.

In some embodiments, the receiving and processing device 30 may further include a network unit connected to the signal processor 33 for receiving and transmitting data through network. The calculated temperature can be sent to other users who are not present during the measurement through network. For example, in the hospital, the nurse or the patient can send the measured temperature to the doctor through network, allowing the doctor to obtain the temperature features of the patient, which is convenient and fast.

Figure 8:
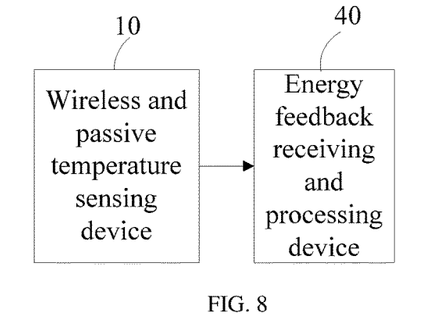
FIG. 8 illustrates a schematic diagram of a system for wirelessly and passively measuring temperature consistent with another embodiment.

Referring to FIG. 8, a system for wirelessly and passively measuring temperature according to another embodiment is provided, including a wireless and passive temperature sensing device 10 and an energy feedback receiving and processing device 40.

As shown in FIG. 2, the wireless and passive temperature sensing device 10 includes a RF receiving circuit 11, a storage capacitor 12, and a crystal oscillator circuit 13. The RF receiving circuit 11 receives an energy feedback RF signal from an energy feedback device, and converts the RF signal to electric energy. The electric energy is stored into/in the storage capacitor 12. After the storage capacitor 12 is conducted, the crystal oscillator circuit 13 is activated to transmit a RF signal under the current temperature to the energy feedback receiving and processing device. The wireless and passive temperature sensing device is configured without a structure for being connected to an external power supply and without space for receiving a battery, thus, the device can have a relatively small size for having less components to be small and portable. This allows the user to place the device on any position such as on the underwear, pants, or the armpit since the device may not affect daily life of the user, which improves the temperature measuring experience of the system.

As shown in FIG. 6, the energy feedback receiving and processing device 40 includes a temperature compensation crystal oscillator 41, a RF power amplifier 22, a RF receiving amplifier 32, and a signal processor 33. The RF signal from the temperature compensation crystal oscillator 41 is amplified by the RF power amplifier 22 and is further transmit to the wireless and passive temperature sensing device. The RF receiving amplifier 32 receives the RF signal under the current temperature from the wireless and passive temperature sensing device and outputs the RF signal to the signal processor 33. The signal processor 33 calculates the current temperature according to the inherent frequency of the temperature compensation crystal oscillator 41 and the received RF signal. The difference between the integration of the receiving and processing device and the energy feedback device provided in the above embodiment and the energy feedback receiving and processing device provided in the embodiment lies in that, the integration of the receiving and processing device and the energy feedback device includes two temperature crystal oscillators 21 and 31, while the energy feedback receiving and processing device only includes one temperature crystal oscillator 41. The temperature compensation crystal oscillator 41 provides the energy feedback RF signal having a special frequency as well as the frequency required by the signal processor 33.

The energy feedback receiving and processing device 40 may further include a network unit connected to the signal processor for receiving and transmitting data through network. Thus, the calculated temperature can be sent to other users who are not present during the measurement through network. For example, in the hospital, the nurse or the patient can send the measured temperature to the doctor through network, allowing the doctor to obtain the temperature features of the patient, which is convenient and fast.

In the above different embodiments, different codes are set to correspond to different wireless and passive temperature sensing devices to represent different users. The receiving and processing device can simultaneously receive signal data from multiple wireless and passive temperature sensing devices. Furthermore, a timer can be disposed inside the energy feedback device, such that the energy feedback device can transmit energy at given time and the wireless and passive temperature sensing device can be started to transmit the RF signal under the current temperature.

In one case, the system for wirelessly and passively measuring temperature as shown in FIG. 7 can be used as follows: the user carries the wireless and passive temperature sensing device 10 secured to the underwear or pants, and the crystal oscillator of the crystal oscillator circuit of the device 10 is in contact with the skin of the user; when measuring the body temperature, the energy feedback device 20 work in a short period to transmit the energy feedback RF signal; the receiving and processing device 30 is started to receive the RF signal under the current temperature sent from the device 10 for analysis; before receiving the RF signal under current temperature sent from the device 10, the receiving and processing device 30 keeps detecting the RF signal; and after receiving the RF signal under the current temperature, the receiving and processing device 30 accurately measures the frequency offset of the RF signal using frequency mixing and frequency discrimination technology and calculates the temperature corresponding to the frequency offset to obtain the user's body temperature, which is convenient and fast. With the system for wirelessly and passively measuring temperature, the user can get new temperature measurement experience and finish the measurement of the body temperature by storing and uploading the measured temperature.

In the above process, since the wireless and passive temperature sensing device 10 can work for 100 milliseconds, and the receiving and process device 30 can be started after the energy feedback device 20 is started to save the frequency resource.

In the above embodiment, the wireless and passive temperature sensing device 10 can be configured with supplementary device such as RFID to finish the temperature measurement better.

The description of the disclosed embodiments is provided to illustrate the present invention to those skilled in the art. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for wirelessly and passively measuring temperature, comprising a wireless and passive temperature sensing device, an energy feedback device, and a receiving and processing device;
    wherein the energy feedback device comprises a first temperature compensation crystal oscillator and an RF power amplifier, and an RF signal from the first temperature compensation crystal oscillator is amplified by the RF power amplifier and is further transmit to the wireless and passive temperature sensing device;
    wherein the wireless and passive temperature sensing device comprises an RF receiving circuit, a storage capacitor, and a crystal oscillator circuit, the RF receiving circuit receiving the RF signal from the energy feedback device and storing energy of the RF signal into the storage capacitor; wherein after a voltage of the storage capacitor reaches a suitable level, the crystal oscillator circuit is activated to transmit an RF signal under a current temperature from the crystal oscillator circuit to the receiving and processing device;
    wherein the receiving and processing device comprises a second temperature compensation crystal oscillator, an RF receiving amplifier, and a signal processor, the RF receiving amplifier receives the RF signal under the current temperature from the wireless and passive temperature sensing device and outputs the RF signal from the wireless and passive temperature sensing device into the signal processor, and the signal processor calculates the current temperature according to an inherent frequency of the second temperature compensation crystal oscillator and the received RF signal under the current temperature.

2. The system according to claim 1, wherein the wireless and passive temperature sensing device comprises a first house, and the RF receiving circuit, the storage capacitor, and the crystal oscillator circuit are configured in the first house; and wherein the first house comprises one side corresponding to the crystal oscillator circuit and made of a thermal conductive material; or, wherein one side of the first house forms an opening through which the crystal oscillator circuit protrudes from the side of the first house.

3. The system according to claim 1, wherein the receiving and processing device further comprises a network unit connected to the signal processor for receiving and transmitting data through network.

4. The system according to claim 1, wherein the first temperature compensation crystal oscillator and the second temperature compensation crystal oscillator are replaced by one third temperature compensation crystal oscillator shared by the energy feedback device and the receiving and processing device.

5. The system according to claim 4, wherein the wireless and passive temperature sensing device comprises a first house, and the RF receiving circuit, the storage capacitor, and the crystal oscillator circuit are configured in the first house; and wherein the first house comprises one side corresponding to the crystal oscillator circuit and made of a thermal conductive material; or, wherein one side of the first house forms an opening through which the crystal oscillator circuit protrudes from the side of the first house.

6. The system according to claim 4, wherein the receiving and processing device further comprises a network unit connected to the signal processor for receiving and transmitting data through network.

\* \* \* \* \*